(12) United States Patent
Hund et al.

(10) Patent No.: US 8,235,951 B2
(45) Date of Patent: Aug. 7, 2012

(54) ATTACHMENT FOR A SYRINGE OR CARTRIDGE

(75) Inventors: Petra Hund, Berg (DE); Joachim Glocker, Weingarten (DE); Walter Schwarz, Bad Waldsee (DE)

(73) Assignee: Arzneimittel GmbH Apotheker Vetter & Co. Ravensburg, Ravensburg (DE)

( * ) Notice: Subject to any disclaimer, the term of this patent is extended or adjusted under 35 U.S.C. 154(b) by 76 days.

(21) Appl. No.: 12/084,758

(22) PCT Filed: Nov. 10, 2006

(86) PCT No.: PCT/EP2006/010791
§ 371 (c)(1),
(2), (4) Date: May 9, 2008

(87) PCT Pub. No.: WO2007/054333
PCT Pub. Date: May 18, 2007

(65) Prior Publication Data
US 2009/0287158 A1   Nov. 19, 2009

(30) Foreign Application Priority Data
Nov. 12, 2005  (DE) .......................... 10 2005 054 075

(51) Int. Cl.
*A61M 5/32* (2006.01)
*A61M 5/00* (2006.01)

(52) U.S. Cl. ........ 604/192; 604/263; 604/187; 604/197; 604/199

(58) Field of Classification Search ................. 604/191, 604/192, 203, 230, 232, 263, 187, 199, 197; 264/328.1; 128/919
See application file for complete search history.

(56) References Cited

U.S. PATENT DOCUMENTS

| | | | |
|---|---|---|---|
| 2,371,086 A * | 3/1945 | Watson et al. ................. 604/192 |
| 2,731,012 A | 1/1956 | Henderson | |
| 2,799,272 A | 7/1957 | Peach | |
| 3,980,083 A | 9/1976 | Elliott | |
| 4,085,737 A * | 4/1978 | Bordow ........................ 600/576 |
| 4,474,734 A * | 10/1984 | Cooper .......................... 422/31 |
| 4,551,138 A | 11/1985 | Shinohara et al. | |
| 4,986,818 A * | 1/1991 | Imbert et al. .................. 604/192 |
| 5,980,495 A * | 11/1999 | Heinz et al. ................... 604/263 |
| 6,000,580 A * | 12/1999 | Nilson .......................... 222/108 |
| 6,053,892 A | 4/2000 | Meyer et al. | |
| 6,485,474 B1 | 11/2002 | Heinz et al. | |
| 6,551,286 B1 | 4/2003 | Claessens et al. | |
| 7,559,919 B2 * | 7/2009 | Pech et al. .................... 604/192 |

(Continued)

FOREIGN PATENT DOCUMENTS

DE  22 54 153 A1  5/1974

(Continued)

OTHER PUBLICATIONS

Japanese Office Action (with English translation) for Japan Patent Application No. 2008-539351, mailed on Oct. 4, 2011.

*Primary Examiner* — Tatyana Zalukaeva
*Assistant Examiner* — Bradley Thomas, Jr.
(74) *Attorney, Agent, or Firm* — Harness, Dickey & Pierce, P.L.C.

(57) ABSTRACT

The invention relates to an attachment for a syringe or cartridge having a cannula, wherein the attachment comprises a sealing element, which is molded onto the cannula.

5 Claims, 8 Drawing Sheets

U.S. PATENT DOCUMENTS

2005/0038391 A1 2/2005 Wittland et al.

FOREIGN PATENT DOCUMENTS

| | | |
|---|---|---|
| DE | 33 11 767 C2 | 10/1984 |
| DE | 41 40 101 C1 | 7/1993 |
| DE | 199 54 373 A1 | 5/2001 |
| DE | 199 55 652 A1 | 6/2001 |
| EP | 0 873 758 A2 | 10/1998 |
| EP | 0 912 209 B1 | 5/1999 |
| EP | 1 502 616 A | 2/2005 |
| FR | 2 522 971 A1 | 9/1983 |
| GB | 868 134 A | 5/1961 |
| GB | 933 587 A | 8/1963 |
| GB | 1 540 881 A | 2/1979 |
| JP | 8033712 A | 2/1996 |
| JP | 10305098 A | 11/1998 |
| JP | 2000354627 A | 12/2000 |
| WO | WO-93/10840 | 6/1993 |
| WO | WO-2006/090118 A | 8/2006 |

\* cited by examiner

ATTACHMENT FOR A SYRINGE OR CARTRIDGE

CROSS-REFERENCE TO RELATED APPLICATIONS

This application is a 371 U.S. National Stage of International Application No. PCT/EP2006/010791, filed Nov. 10, 2006. This application claims priority to German Patent Application No. DE 10 2005 054 075.9, filed Nov. 12, 2005. The disclosures of the above applications are herein expressly incorporated by reference.

The invention relates to an attachment for a syringe or cartridge according to the preamble of claim 1, and to an attachment for a syringe or cartridge according to the preamble of claim 4, furthermore to a method for producing an attachment for a syringe or cartridge according to claim 19, to a method for producing an attachment for a syringe or cartridge according to the preamble of claim 22, furthermore to a syringe or cartridge according to claim 25, and finally to a syringe or cartridge according to claim 26.

Attachments and the production thereof as well as syringes or cartridges having attachments are known. The attachments comprise a sealing element, which serves the tight sealing of the syringe or cartridge such that the content thereof can be stored for extended periods without resulting in contamination, particularly from bacteria, viruses, or the like. It has been found that in many cases the material of the sealing element in the contact region with the syringe or cartridge changes such that microbiological impermeability cannot be guaranteed.

It is therefore the object of the invention to create an attachment that is not associated with these disadvantages.

In order to achieve this task, an attachment is created, which has the characteristics described in claim 1. It comprises a sealing element, which closes and seals the cannula. It is characterized in that the sealing element is molded onto the cannula. In this way, it is possible to guarantee particularly good sealing of the outlet of the cannula, so that even in the event of long-term storage of the syringe or cartridge microbiological contamination of the content is prevented.

According to a preferred embodiment of the attachment, a cap can be placed on the sealing element, the cap protecting the sealing element from mechanical damage.

An attachment comprising a cap that can be molded onto the sealing element is particularly preferred. In this way, a particularly easy connection between the cap and sealing element is guaranteed, and simple production is possible.

In order to achieve this task, also an attachment is proposed, which has the characteristics of claim 4 and is provided with a base body for a syringe or cartridge and with a projection for fastening the attachment and which further comprises a cap and a sealing element. The attachment is characterized in that the sealing element and the cap are connected to one another by an injection molding method. The connection of the two parts is thereby possible in a particularly simple and cost-efficient manner.

Further embodiments will be apparent from the subordinate claims.

In order to achieve this task, also a method for producing an attachment for a syringe or cartridge having the characteristics according to claim 19 is proposed, comprising the following steps: A cannula is seized at the end thereof not serving injection purposes. A sealing element is then molded onto the free end, which is to say the end serving injection purposes. The method is characterized in that it is particularly easy and cost-efficient to implement.

According to a preferred embodiment of the method, a cap is placed on the sealing element in order to guarantee mechanical protection for the sealing element.

In a particularly preferred method, a cap is molded onto the sealing element. Connecting the sealing element and cap using an injection molding method provides for a particularly simple and cost-efficient implementation.

In order to achieve this task, also a method for producing an attachment for a syringe or cartridge, having a base body and a projection for fastening the attachment, is proposed, wherein the attachment comprises a cap and a sealing element. The method with the characteristics according to claim 22 is characterized in that the sealing element and the cap are connected to one another by means of an injection molding method, which is particularly simple and cost-efficient. At the same time, it is guaranteed that the sealing element closes and seals the syringe or cartridge particularly well and protects it from contamination.

Further embodiments of the method will be apparent from the dependent claims.

In order to achieve this task, furthermore a syringe or cartridge according to claim 25 is proposed, which comprises an attachment of the kind described above. The syringe or cartridge is characterized in that the content thereof is protected particularly well from contamination.

Finally, in order to achieve this task, a syringe or cartridge according to claim 26 is proposed, which comprises an attachment that is produced according to any one of the above method.

The invention will be explained in more detail hereinafter with reference to the attached figures, wherein.

Figure 1:
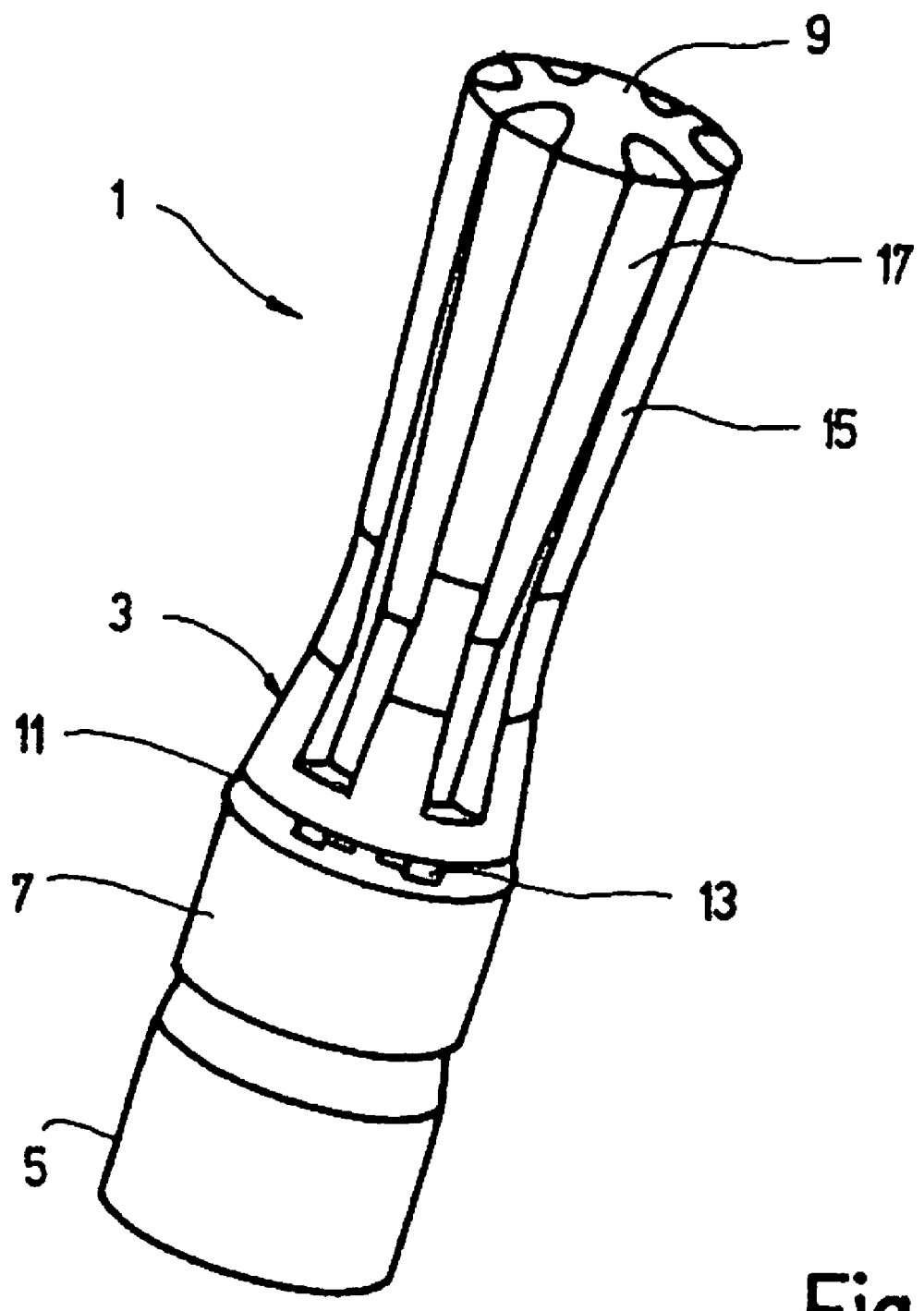
FIG. 1 is a perspective view of a first embodiment of an attachment.

The perspective view in FIG. 1 of an example of an attachment 1 referred to as a cannula attachment comprises a cap 3 serving as a protective cap, which is placed on a syringe 5 made of plastic or preferably glass. The cap 3 has a two-part design and encompasses a retaining region 7, which is attached directly to the syringe 5, and a cap element 9. The two parts are connected to one another by a predetermined breaking line 11, which is known in principle and serves the easy separation of the cap element 9 from the retaining region 7 and therefore from the syringe 5. The predetermined breaking line is spanned by retaining members 13, which connect the cap element 9 and the retaining region 7 with each other, but are configured weak enough to separate the cap element 9 from the retaining region 7 by a tilting, pulling or rotating motion. As a result, the cannula located beneath the cap 3 is exposed. During initial opening, the predetermined breaking line 11 bursts open, so that manipulations are immediately apparent. The cap 3 therefore serves a tamper-proofing element.

The cap element 9 comprises a plurality of webs 15 extending in the longitudinal direction of the element, wherein the webs are disposed at a distance from each other and hold a first sealing element 17 identified as the protective cap. This element is preferably made of rubber or TPE, which is to say a thermoplastic elastomer. It has particularly good grip properties and closes the free end of the cannula, which is not shown here. The first sealing element 17 is integrally formed on the cannula, preferably by injection molding. The cap 3 can then be placed on the first sealing element 17. It is possible, however, to mold the cap 3 onto the sealing element 17, which is to say produce it in an injection molding process, in order to establish a connection between the cap 3 and sealing element 17. The cap 3 as such may in principle also comprise rubber or TPE or can be made of one or two of the above materials. In general, however, it comprises hard plastic material or is preferably made of this material. The cap 3 and the first sealing element 17 are preferably produced in a two-component injection molding process.

Particularly preferred is an embodiment of the attachment 1, wherein the sealing element 17 in the contact region with the syringe or cartridge comprises TPE or rubber or is made of TPE or rubber in order to guarantee optimized sealing of the syringe or cartridge. These materials have the characteristic that they do not run even in the case of extended storage of the syringe or cartridge, thereby ensuring a microbiologically safe sealing of the syringe or cartridge. The cap 13 is preferably made of hard plastic and protects the sealing element 17 during storage and transport of the syringe or cartridge. The cap 13 is particularly easy to remove if it is provided with a predetermined breaking line 11. This line, however, can also be foregone and the attachment 1 can be removed as a whole from a syringe or cartridge.

Figure 2:
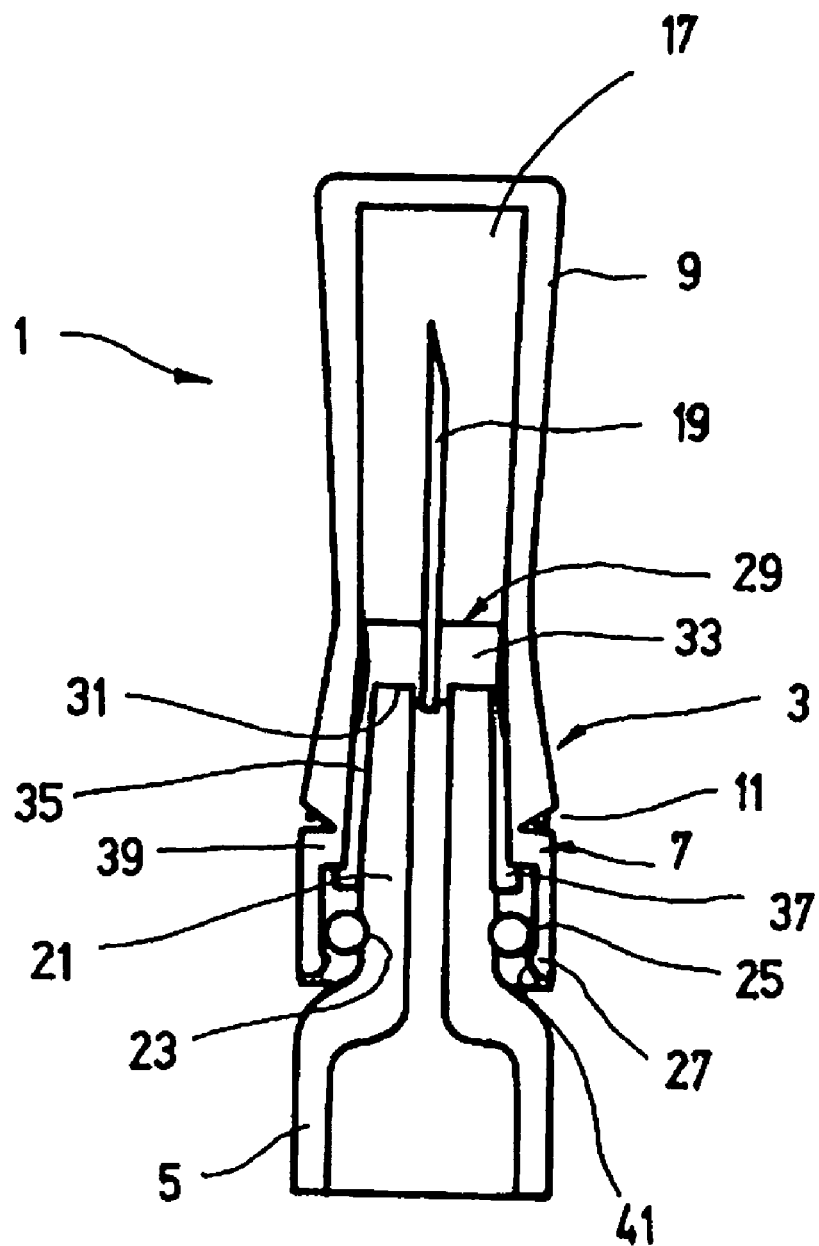
FIG. 2 is a longitudinal sectional view of the attachment shown in FIG. 1.

The first embodiment of the attachment 1 is shown in a longitudinal sectional view in FIG. 2. Identical parts have been identified with identical reference numerals, so that in this respect only reference is made to the preceding figure.

The figure clearly shows the cap 3 with the cap element 9 and the retaining region 7, which is connected to the cap element 9 via the predetermined breaking line 11.

It is apparent here that the cannula 19 is disposed in the first sealing element 17, which acts and serves as protection for the needle.

The sectional view according to FIG. 2 shows that the syringe 5 comprises a projection 21 configured as a Luer-type fitting, onto which the attachment 1 is placed.

The projection 21 may be provided with an annular groove 23, in which a retaining ring 25 engages, which is thereby safely held viewed in the axial direction of the projection 21. The retaining region 7 extends across the retaining ring 25 and is safely held thereon by means of at least one catch lug 27. Instead of the at least one catch lug 27, also an enclosed inwardly projecting catch ring may be provided.

The cannula 19 is provided in a cannula lift 29, which is also referred to as a cannula holder and comprises a base plate 33 disposed between the first sealing element 17 and the face 31 of the projection 21, wherein the base plate forms the bottom of the substantially cup-shaped cannula lift and a cylindrical or slightly conical wall 35 extends therefrom. At the end of the wall 35 facing away from the base plate 33, a peripheral, outwardly projecting edge 37 is provided, which rests underneath a peripheral shoulder 39, which projects radially inward from the retaining region 7 and thereby safely holds the edge 37, which is to say the cannula lift 29.

Viewed from the syringe 5, the predetermined breaking line 11 is provided above the shoulder 39 such that, when the cap element 9 is broken off, turned off or pulled off the retaining region 7, the cannula lift 29 is still held safely on the syringe 5 because the catch lug 27 is still anchored beneath the retaining ring 25.

The illustration shows that the catch lug 27—or the catch ring—comprises an inwardly facing slanted region 41 such that the attachment 1 can be easily placed on the syringe 5, wherein the catch lug 27 then engages beneath the retaining ring 25.

The cannula lift 29 preferably comprises rubber or TPE, in particular it is made of rubber or TPE, because in this way optimum sealing of the syringe 5 is guaranteed.

Figure 3:
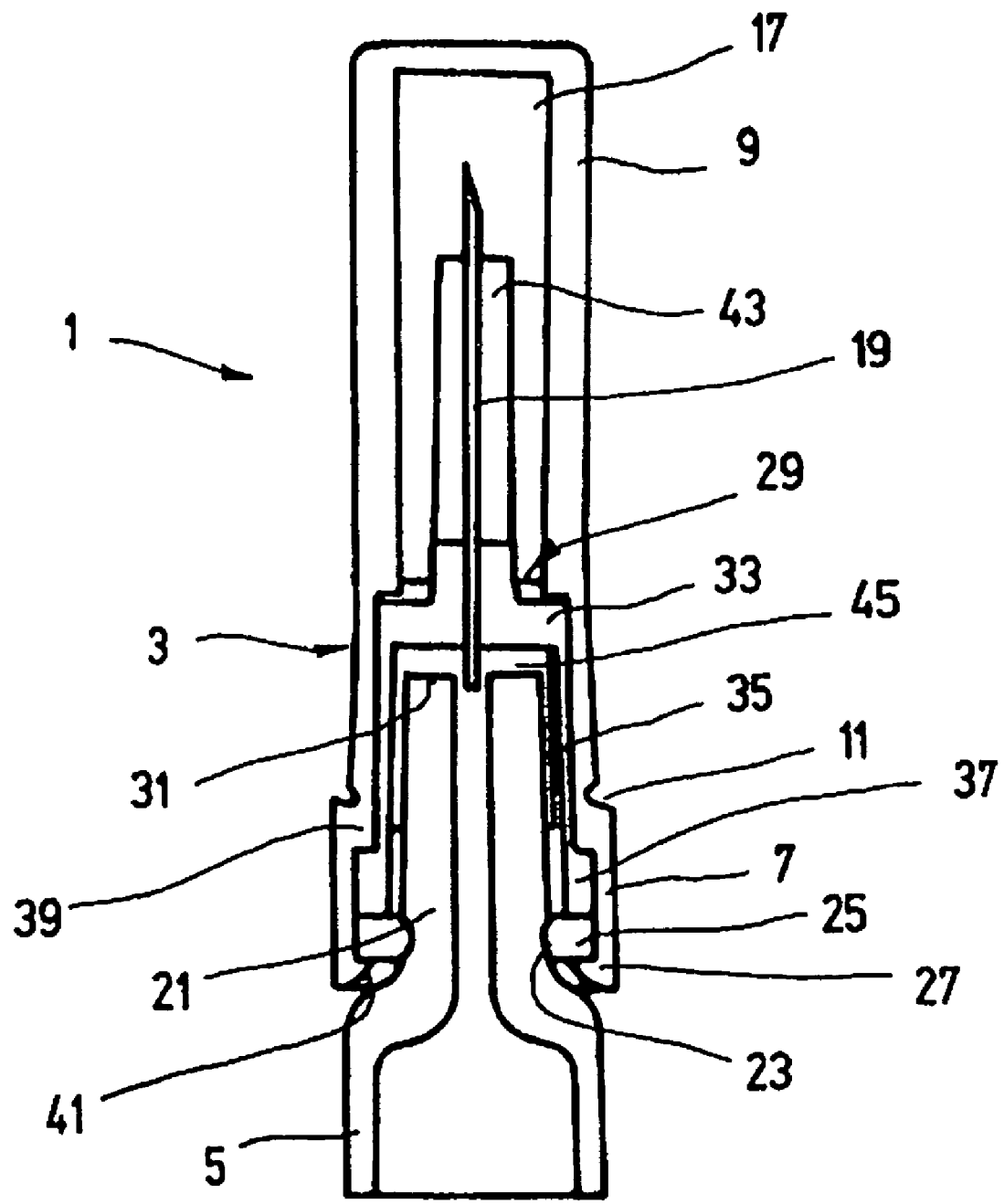
FIG. 3 is a longitudinal sectional view of a second embodiment of an attachment.

FIG. 3 shows a longitudinal sectional view of a modified example of an attachment 1. Identical parts have been identified with identical reference numerals, so that in this respect only reference is made to the description of the preceding figures.

The longitudinal sectional view shows that a cap 3 is again placed on the syringe 5, wherein the cap comprises a retaining region 7 facing the syringe 5 and a cap element 9 connected thereto via a predetermined breaking line 11, with a first sealing element 17 being provided in the cap element. The sealing element in this example encompasses a hollow space 43, which does not extend across the entire length of the cannula 19 protruding from the cannula lift 29. The end of the cannula facing away from the cannula lift 29, however, is located inside the first sealing element 17.

It is also apparent from the illustration that the cannula hub does not rest directly against the face 31 of the projection 21. Rather, a second sealing element 45 is provided here, which extends like a cap across the region of the projection 21 adjoining the face 31.

The second sealing element 45 preferably comprises rubber or TPE or is made of rubber or TPE. As a result of the direct contact of the elastic material of the second sealing element 45 with the syringe 5, particularly good sealing of the syringe 5 is achieved. In principle, it is also possible to use hard plastic for the second sealing element 45. However, since this material changes, which is to say runs, the sealing properties are not ideal. Therefore, an attachment 1 is proposed here, wherein during storage a product in the syringe 5 or cartridge only comes in contact with glass or steel, or with the second sealing element 45 made of rubber or TPE.

Since the second sealing element 45 is elastic and guarantees optimum sealing of the syringe 5, the cannula lift 29 can certainly be made of hard plastic.

In this example, the cannula lift 29 comprises a base plate 33 and a peripheral wall 35 extending therefrom, which at the end thereof facing away from the base plate 33 has a rim 37, which is held by a peripheral shoulder 39 of the retaining region 7. As is shown in the example according to FIG. 2, instead of the peripheral shoulder 39 only individual protrusions may be provided to fix the cannula lift 29 in place.

Again, the projection 21 is provided with a peripheral annular groove 23, in which a retaining ring 25 engages. The cap 3 is again held on the retaining ring 25 by at least one catch lug 27 or by a peripheral catch ring.

It is also provided here that the catch lug 25 comprises a slanted region 41, thus facilitating the placement of the attachment 1.

For the examples illustrated here, a separate retaining ring 25 has been described. It is certainly possible to integrate it in the cannula lift 29, which is to say to produce the retaining ring 25 and the cannula lift 29 as one piece. In this case, the lower edge of the cannula lift 29 facing the syringe 5 is provided with an inwardly projecting annular bead 15 acting as a retaining ring 25.

Figure 4:
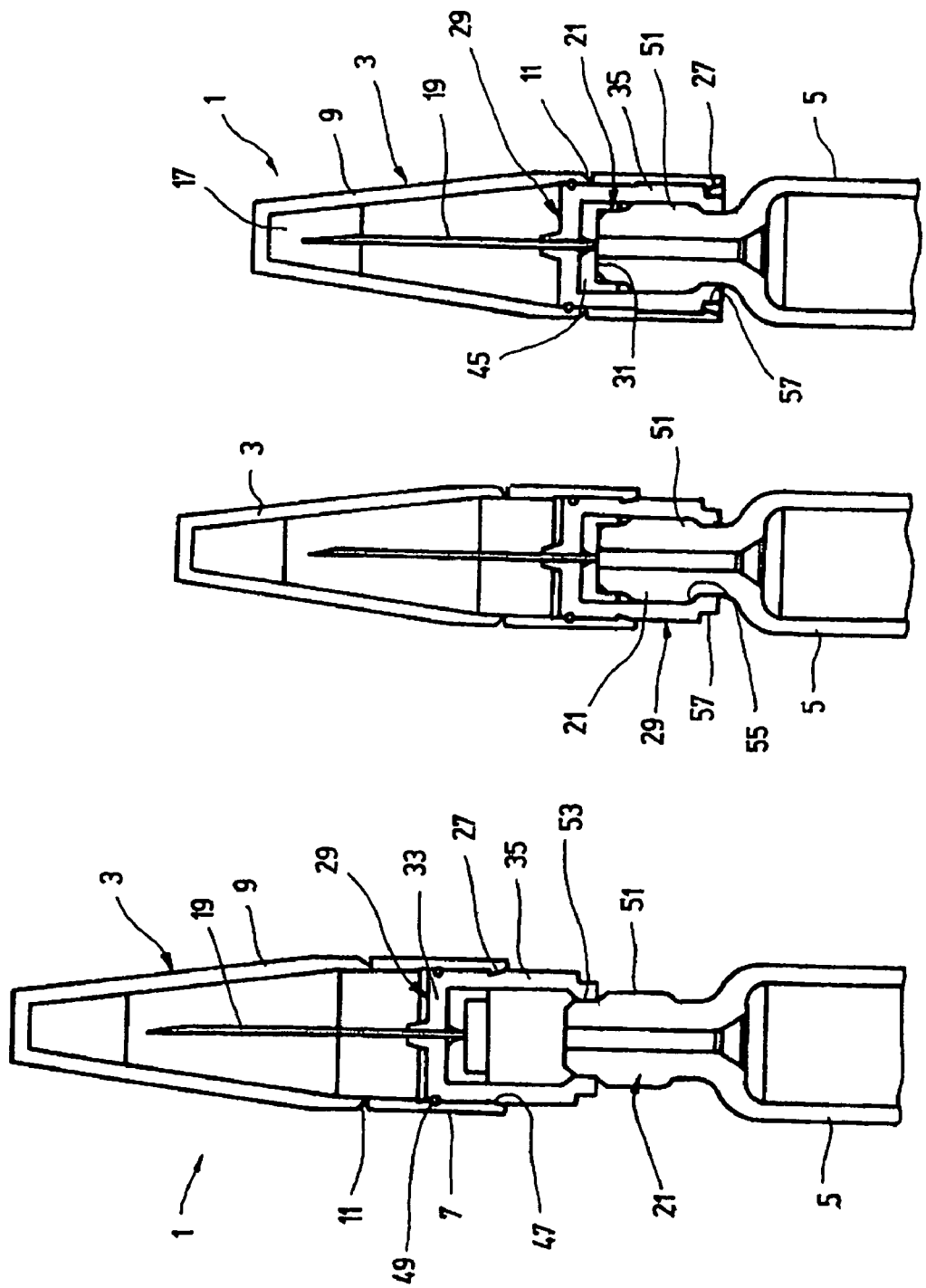
FIG. 4 is a third embodiment of an attachment, in three assembly positions.

FIG. 4 shows a further example of an attachment 1 in three different assembly positions. Identical parts have been identified with identical reference numerals, so that in this respect only reference is made to the preceding description.

The attachment 1 comprises a cap 3, which is provided with a cap element 9 and a retaining region 7 connected thereto by a predetermined breaking line 11. A cannula 19 is provided in a cannula lift 29, preferably by molding, wherein the lift again comprises a base plate 33, from which preferably a peripheral wall 35 extends.

At the lower edge region facing the syringe 5, the retaining region 7 comprises at least one catch lug 25, preferably a peripheral, radially inwardly projecting catch ring, which engages in an annular groove 47 provided on the outer surface of the cannula lift 29. In addition, a sealing device may be provided between the inside of the retaining region 7 and the outer surface of the cannula lift 29, wherein in this example the device is configured as an O-ring 49. It protects the cannula 19 during storage.

In the left illustration in FIG. 1, the attachment 1 is placed on the projection 21 of the syringe 5, wherein in this example the projection has at least one radially outwardly projecting protrusion, preferably an annular bead 51, whose outside diameter is larger than the inside diameter of the wall 35 on the end facing away from the base plate 33, where a retaining device for the cannula lift 29 is configured, in this example an inwardly projecting, preferably annular protrusion 53.

In the second assembly position shown at the center of FIG. 4, the conical attachment 1 has been pressed downward in the direction of the syringe 5 such that the cannula lift 29 encompasses the annular bead 51, wherein the protrusion 53 engages beneath the annular bead 51, which is to say on the outer shoulder 55 facing the syringe 5. The protrusion 53 thereby acts as a retaining ring, which engages in a groove disposed beneath the annular bead 51. The illustration shows that, in this second assembly position, no relative displacement has occurred between the cap 3 and the cannula lift.

The third assembly position is shown on the right of FIG. 4. The attachment 1 has been completely mounted on the syringe 5 in that the cap 3 was completely shifted downward, which is to say in the direction of the syringe 5, such that at least the catch lug 27 of the retaining region 7 of the cap 3 engages beneath the cannula lift 29. On the outside of the retaining region, a corresponding annular groove 57 is provided, in which the catch lug 27 can engage.

In this assembly position, the retaining region 7 encompasses the wall 37 of the cannula lift 29 from the outside and thereby secures the cannula lift 29 on the outside shoulder 55 of the projection 21 such that manipulations on the conical attachment 1 are immediately apparent to a user. If a user applies a lateral force, or a tensile or rotary force, on the cap element 9, the predetermined breaking line 11 breaks, or the retaining members 13 provided thereon break, which are not shown here. The cap element 9 detaches from the retaining element 7, which is immediately apparent to a user. As a result, a tamper-proofing element or manipulation safety device is implemented.

In the cap element 9, a first sealing element 17 is provided on the inside on the end facing away from the cannula lift 29. The sealing element extends—viewed in the longitudinal direction of the cap element 9—in a region, which is selected such that in the third assembly position the cannula 19 is embedded in the first sealing element 17.

The first sealing element 17 preferably comprises rubber or TPE, or is made of rubber or TPE. The cap 3 can likewise comprise or be made of these materials. Preferably, however, it is made of hard plastic in order to provide the attachment 1 with greater stability and protect the sealing element.

The cannula lift 29 may comprise rubber or TPE, or it can be made of one or both of these materials, in order to guarantee optimized sealing in relation to the projection 21 of the syringe 5. A configuration of this type was explained with reference to FIG. 2.

As was explained above with reference to the example according to FIG. 3, a second sealing element 45 may be provided between the cannula lift 39 and the face 31 of the projection 21. This is shown in FIG. 4. The second sealing element 45 is preferably optimally configured to act as a seal between the attachment 1 and syringe 5 and therefore comprises rubber or TPE, or is made of rubber or TPE.

In the example shown in FIG. 4, the cannula lift 29 is integrally formed on the cannula 19, which is to say produced using an injection molding method, and molded onto the cannula 19. It is also possible without difficulty to attach it to the cannula by gluing. The second seal 45 may be inserted, or preferably molded, in the cannula lift, wherein then the cannula lift 29 and the second seal 45 are preferably produced using a two-component molding process.

The first sealing element 17 may be inserted in the cap 3, or it may be produced by means of an injection molding method and molded into the cap 3. According to a particularly preferred embodiment, the cap 3 and the first sealing element 17 are produced in a two-component injection molding process and molded onto the cannula 19.

It is apparent from the explanations for FIG. 4 that the cap 3 and the cannula lift 29, which may optionally also encompass the second sealing element 45, are produced separately.

In producing the attachment 1, initially two separate elements can be manufactured, which is to say the cannula lift 29, which is preferably provided with the second sealing element 45, and the cap 3 having the first sealing element 17.

When producing the cannula lift 29, the cannula lift 29 is preferably integrally formed on the cannula 19, particularly molded thereon, while the cannula 19 is held at the free end thereof. Thereafter, the second sealing element 45 may be inserted in the cannula lift 29. It is preferred, however, insofar as the second sealing element 45 is provided, to produce both parts, which is to say the cannula lift 29 and the second sealing element 45, using a two-component injection molding method. It is apparent in this example that in a very simple case the cannula 19 can also simply be glued into the cannula lift 29.

Accordingly, the cap 3 is preferably produced using an injection molding method, wherein preferably the first sealing element 17 and the cap 3 are connected to one another by injection molding. Provided that the cap and the sealing element are made of different materials, which is a preferred embodiment, the two parts are preferably manufactured using a two-component injection molding method.

When looking at the examples illustrated in FIGS. 1 to 3 and the example in FIG. 4 in the third assembly position shown on the very right of FIG. 4, the following is apparent with respect to the production of the attachment 1:

The cannula 19 can be seized at the end thereof serving injection purposes, which is disposed at a distance to the syringe. The opposite end may be formed in a cannula lift 29. The cannula lift 29 is integrally formed on the free end by means of an injection molding method, wherein the cannula lift 29 as such is produced at the same time. It is also possible to glue the cannula in the cannula lift.

At this time, or later, a second sealing element 45 may be inserted or molded into the cannula lift 29. Preferably, however, it is provided to integrally form both the cannula lift 29 and the second sealing element 45 on the free end of the cannula 19 using a two-component injection molding method, which is to say to produce the two parts at the same time.

The end of the cannula 19 serving injection purposes is now exposed. The cannula 19 can be held in a region at a distance to the end serving injection purposes, or on the cannula lift 29. Now, a first sealing element 17 can be integrally formed, preferably molded, onto the free end of the cannula 19. With this production method, the cannula tip cannot be damaged. On the other hand, damage is quite possible when piercing a sealing element with the cannula, for example the tip of the cannula could become bent and form a barb.

Subsequently, the cap 3 can be placed on the first sealing element 17. The cap 3, however, is preferably integrally formed using an injection molding method, and is molded onto the first sealing element 17 and the cannula lift 29.

A method, wherein the first sealing element 17 and the entire cap 3 are integrally formed, preferably molded, onto the free end of the cannula 19 serving injection purposes using a two-component molding method, is particularly preferred.

The finished, which is to say pre-assembled, attachment 1 can now be placed on a syringe 5, wherein if necessary a retaining ring 25 is used, as that described based on the explanations of FIGS. 2 and 3. The retaining ring 25 can initially be fastened to the projection 21 of the syringe 5, or it can be introduced into the open end of the attachment 1 or of the cannula lift 29. Finally, the retaining ring 25 may also be implemented as part of the cannula lift 29.

It is apparent from the explanations regarding FIGS. 1 to 4 that the production method is very simple and variable. For example, if the cannula lift 29 is made of a soft material, a second sealing element 45 can be foregone. It can also be inserted, or preferably molded, into the cannula lift 29. It is particularly preferred to produce the cannula lift 29 and the second sealing element 45 using a two-component injection molding method.

The configuration of the individual parts of the attachment 1 can also be selected freely to a great extent. It is therefore possible, for example, to produce caps 3 having webs 15, which were explained based on FIG. 1. Since in this configuration the first seal 17 is accessible from the outside by the intermediate spaces of the webs 15, the cap 3 and the cap element 9 have particularly good grip properties, which improves the handling of the attachment 1 when a soft non-slip material, such as rubber or TPE, is used for the first sealing element 17.

The production of other configurations of the cap 3, for example of a cup-shaped, completely enclosed cap having a conical outer surface, is possible without difficulty. Such a configuration is shown in FIG. 4.

Incidentally, it has been shown that the cannula lift can also have different configurations. It can, for example, be provided with a base plate 33, as is described here. A wall 35 extending therefrom may comprise individual retaining arms disposed adjacent to one another, or even be a completely enclosed wall 35. At the end of the cannula lift 29 facing the syringe 5 in the assembled state, locking devices are provided, in the example at least one catch lug 27, which securely hold the cannula lift 29, and consequently the attachment 1, on the projection 21 of a syringe 5. A comparison of the configurations of the projections shown in FIGS. 1 to 3 and 4 illustrates that the attachment 1 can be combined with a variety of syringe arrangements.

Through the selection of the materials for the cap 3, the cannula lift 29, the first sealing element 17, and for the preferably provided second sealing element 45, the characteristics of the attachment 1 can be adjusted to the requirements, the handling and sealing effect in relation to the cannula 19 and syringe 5 within a broad range. For example, it is possible to combine hard and soft materials and jointly process them using a two-component injection molding method.

If the material for the cannula lift 29 is selected appropriately, it is also conceivable to siliconize the cannula 19 after attaching the cannula lift 29. As a result, an attachment 1 is created, which can be adapted to a variety of application purposes.

By integrally forming the first seal 17 on the end of the cannula 19 serving injection purposes, it is ensured that the end is not damaged, and in particular it is prevented that barbs are formed. In addition, bending of the cannula 19 is prevented very reliably.

Figure 5:
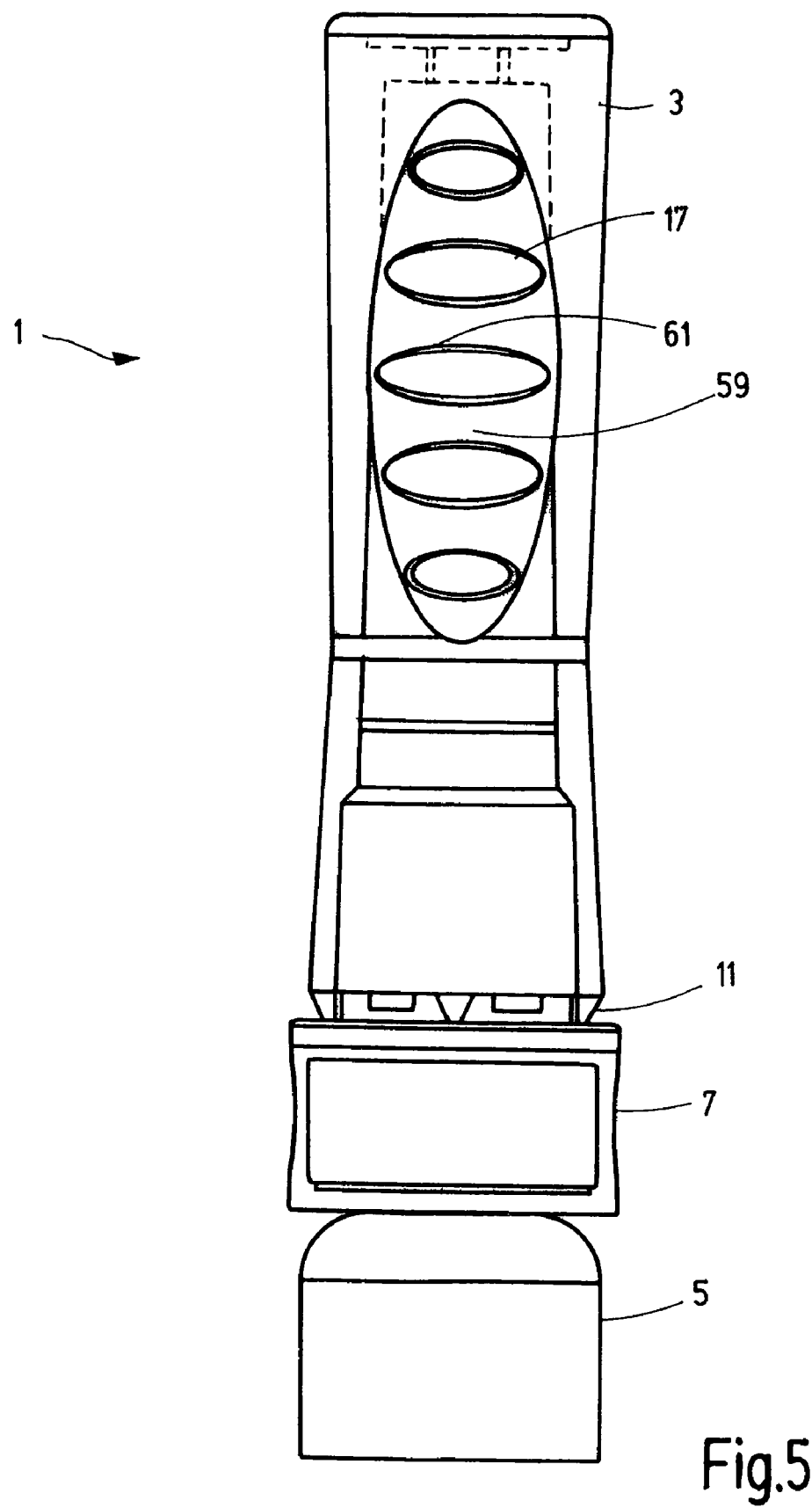
FIG. 5 is a side view of a modified embodiment of an attachment.

FIG. 5 shows a modified example of an attachment 1 in a side view. It comprises a cap 3, which is preferably made of a hard plastic and encompasses a sealing element 10, which is made of rubber or preferably TPE, or comprises at least one or both of these materials. In the illustrated example, the cap 3 is connected via a predetermined breaking line 11 to a retaining region 7, which is provided on a syringe 59. It is certainly possible to configure the attachment 1 without such a predetermined breaking line 1 and fasten it directly to the syringe 5.

The cap 3 has a substantially cylindrical configuration. At the circumferential surface thereof, it comprises one, preferably two opposing flattened regions 59, which improve the grip properties of the cap 3. In the example illustrated here, the cap 3 is provided with at least one aperture 61 in the flattened regions 59, wherein the sealing element 17 comes in contact with the attachment 1 when the fingers of the user seize the cap 3. Since the sealing element 37, as was explained above based on the described examples, is made of rubber or preferably TPE, the grip properties of the cap 3 are considerably improved.

In the example illustrated here, a plurality of superimposed apertures 61 are provided, which have an elliptic configuration viewed from above, wherein the larger diameter line extends transversely to the longitudinal axis of the attachment 1 and/or of the cap 3. Since the flattened region 59, viewed across the length thereof, which is to say the height according to FIG. 5, first has an increasing and then a decreasing depth, the width of the apertures 61, viewed across the height of the flattened region 59, is not the same, but rather is larger at the center than it is at the top and bottom, because the flattened region 59 has a symmetrical configuration.

Figure 6:
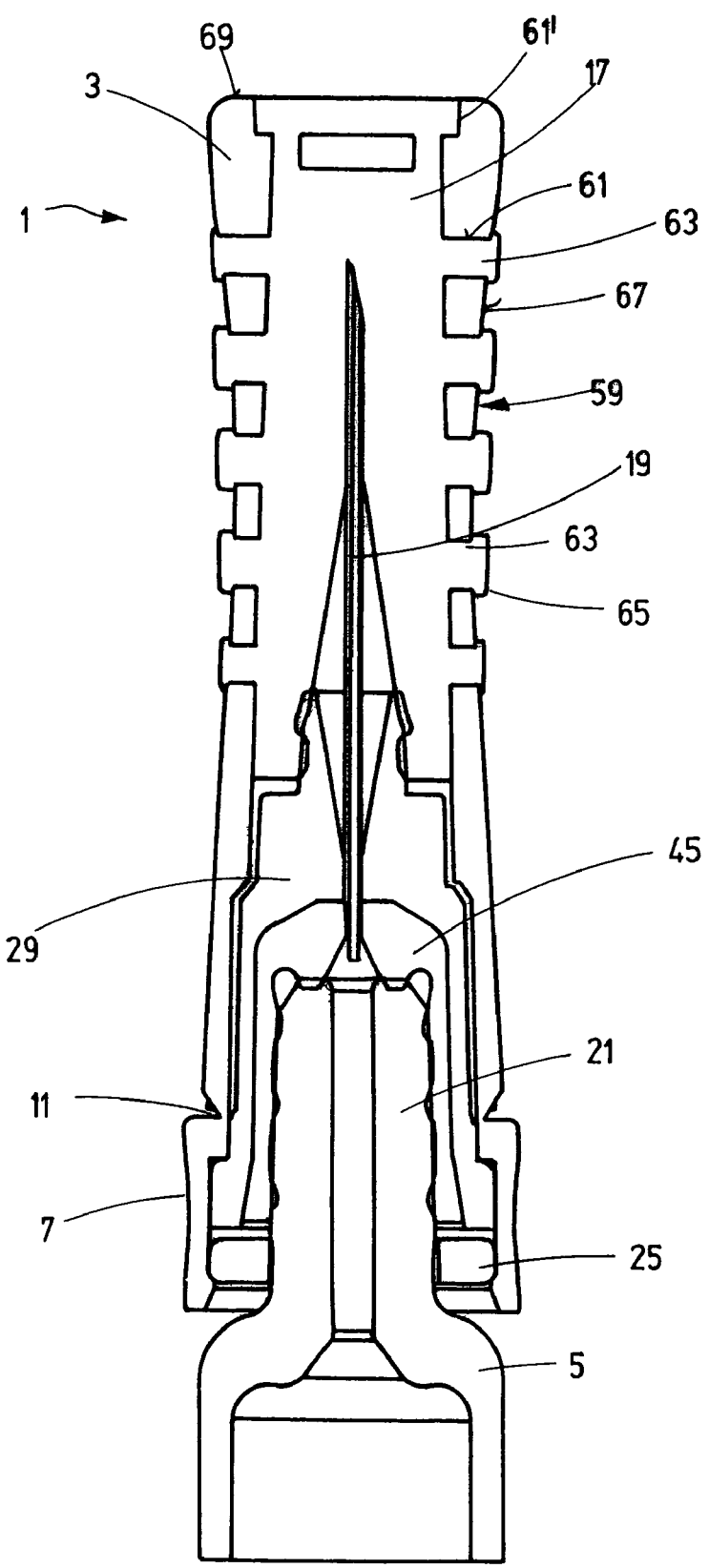
FIG. 6 is a longitudinal sectional view of the attachment according to FIG. 5.

FIG. 6 shows the attachment according to FIG. 5 in a longitudinal sectional view. It is apparent that it comprises a cap 3, which transitions into the retaining region 7 via the predetermined breaking line L. As was explained above based on FIG. 2, this region is fixed to a projection 21 of the syringe 5 via a retaining ring 25. The ring holds a cannula lift 29, into which a cannula 19 is preferably glued. It is also conceivable, however, to integrally form the cannula lift 29 on the cannula 19, in particular mold it thereon.

The cannula lift 29 encompasses the projection 21 of the syringe 5 in a cap-like manner. As was already explained based on FIG. 3, a second sealing element 45 is introduced, preferably molded, into the interior of the cannula lift, wherein the element is made of rubber or TPE, or comprises these substances. The second sealing element 45 encompasses the circumferential surface of the projection 21 and rests against the face thereof in a sealing fashion, thus guaranteeing ideal closure.

The first sealing element 17 is molded into the upper end of the cap 3, which is provided opposite the projection 21 and/or the retaining region 7. It is apparent in this example that the material of the first sealing element 17 penetrates the apertures 61, wherein webs are formed, which guarantee a positive fit between the cap 3 and sealing element 17. A circle indicates that the webs in the end regions 65 thereof slightly project beyond the outer surface 67 of the cap 3, in this example the flattened region 59. The webs 63 have a quasi T-shaped configuration in their cross-section. On the one hand, this produces a secure connection between the cap 3 and the sealing element 17; on the other hand, it slightly increases the surface formed by the sealing element 17 for seizing the cap 3, which is to say it is larger than the associated apertures 61. In the illustrated example, an aperture 61' is also provided in the region of the face 69, wherein the first sealing element 17 extends in this region to the face 69, which is to say it forms part of the outer surface of the cap 3.

This embodiment serves the implementation of the largest possible region of the outer surface of the cap 3 by the first sealing element 17, as is provided already in the example according to FIG. 1. Since particularly TPE is permeable to vapor, the use of this material the large outer surface of the first sealing element 17 enables optimum final sterilization or terminal sterilization of the attachment 1. The vapor can penetrate into the interior of the attachment 1, thus guaranteeing ideal sterilization even there.

Since the first sealing element 17 is made of rubber, or preferably made of TPE, the cannula 19 is tightly sealed, so that microbiological contamination of the content of the syringe 5 is practically excluded. The direct outlet of the syringe 5 in the region of the projection 21 is sealed by the second sealing element 45 in the example illustrated here.

Figure 7:
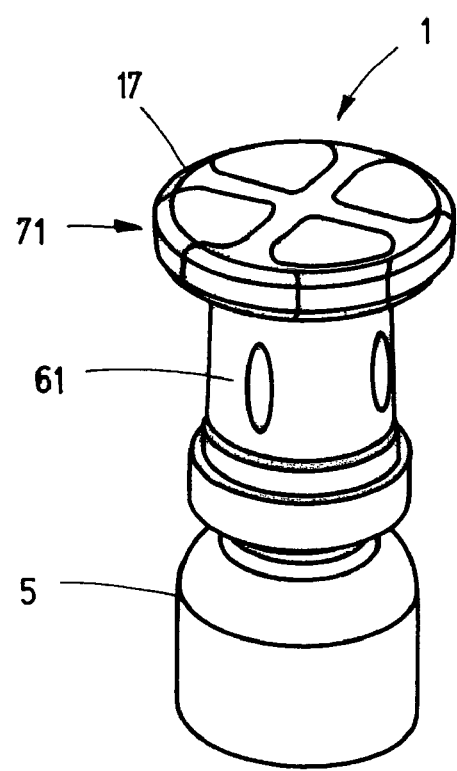
FIG. 7 is a perspective view of a modified embodiment of an attachment.

FIG. 7 shows a modified example of an attachment 1, which comprises a cylindrical base body encompassing a projection of a syringe 5 and ends in a widened head 71 at the end facing away from the syringe 5.

Again, at least one, preferably a plurality of apertures 61 are distributed across the circumferential surface of the attachment 1, wherein the apertures are filled with the material of the first sealing element 17. The element thus extends to the outer surface of the attachment 1. The darker regions of the head 71 indicate that the material of the first sealing element 17 extends also here to the outer surface of the attachment 1. As a result, the grip properties of the attachment 1 are improved, and additionally parts of the outer surface of the attachment 1 are formed by the vapor-permeable material of the sealing element 17 such that vapor can penetrate into the inside of the attachment 1 and contribute to the sterilization of the attachment 1 on the syringe 5.

Figure 8:
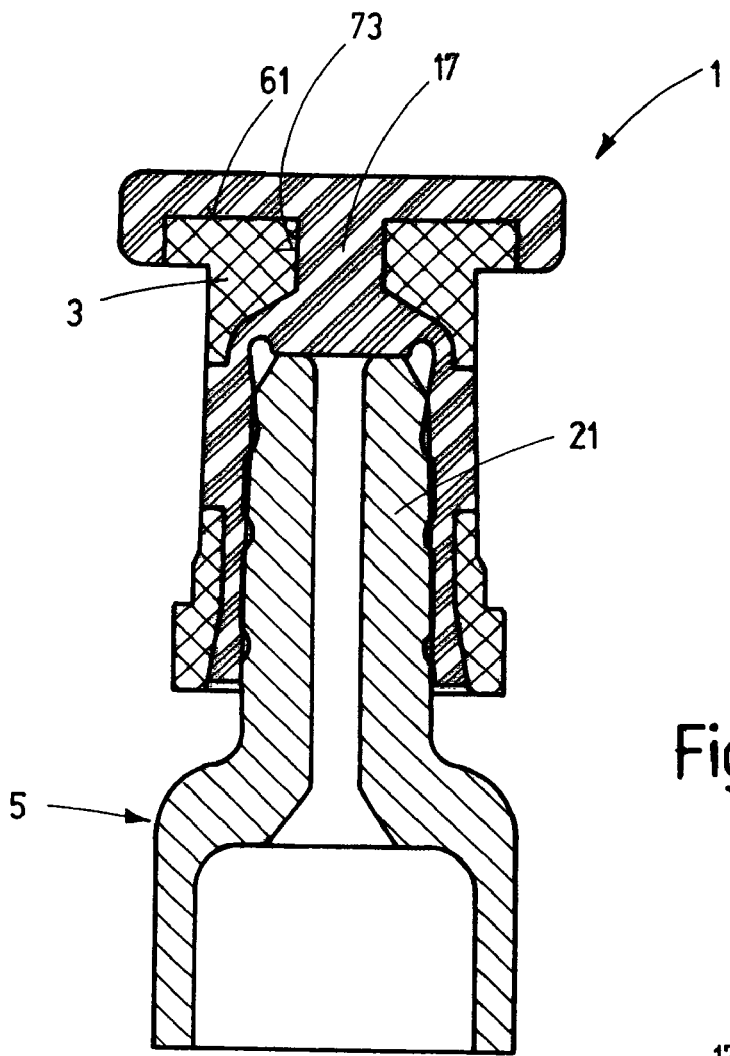
FIG. 8 is a longitudinal sectional view of the example according to FIG. 7.

Based on FIG. 8, which shows a longitudinal sectional view of the embodiment according to FIG. 7, it is apparent that the sealing element 17 encompasses the projection 21 of the syringe 5 and fills the inside of the cap 3. It is also apparent that the material of the sealing element 17 extends to the outer surface of the cap 3 in order to, as explained above, improve the grip properties of the attachment 1 and optimize sterilization.

In the example illustrated here, a central opening 73 is provided in the region of the face 69 of the cap 3, wherein the material of the sealing element 17 protrudes upward via said opening from the inside of the cap 3 and can form the outer surface of the cap 3. FIG. 7 illustrates that the sealing element 17 forms two vertically stacked webs extending along a diameter line, wherein the webs widen in the region of the circumferential surface of the head 71 in order to enlarge the grip regions.

The number of webs and grip regions as well as that of the apertures can be selected within a wide range.

The essential aspect here, as with all other embodiments of the attachment 1, is that the sealing element 17 is preferably molded into the cap 3 in order to guarantee a secure connection between the cap and sealing element, and additionally in order to guarantee optimized microbiological sealing of the syringe 5.

The cap 3 is preferably always made of a hard plastic, or comprises such a plastic material, and the sealing element 17 as well as the second sealing element 45 are made of a softer material, preferably rubber or particularly TPE. TPE is preferably selected at a hardness of 30 to 60 Shore A. On the one hand, this guarantees optimum adaptability of the sealing elements to the surface of the regions to be sealed, on the other hand, it ensures sufficient stability and grip properties of the attachment 1.

Figure 9:
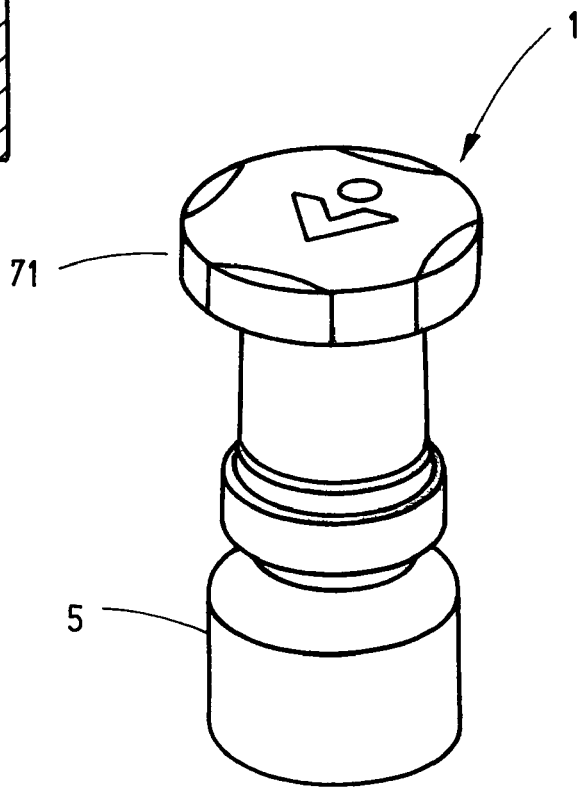
FIG. 9 is a perspective view of a modified embodiment of an attachment.

FIG. 9 shows a modified example of an attachment 1, which is placed on a syringe 5. Again, as in FIG. 7, a quasi mushroom-shaped attachment 1 provided, whose cylindrical base body encompasses a projection of the syringe 5 and which comprises a head 17 at the end facing away from the syringe. The outer region of the head is again provided with the material of the sealing element in order to improve the grip properties of the attachment 1.

Figure 10:
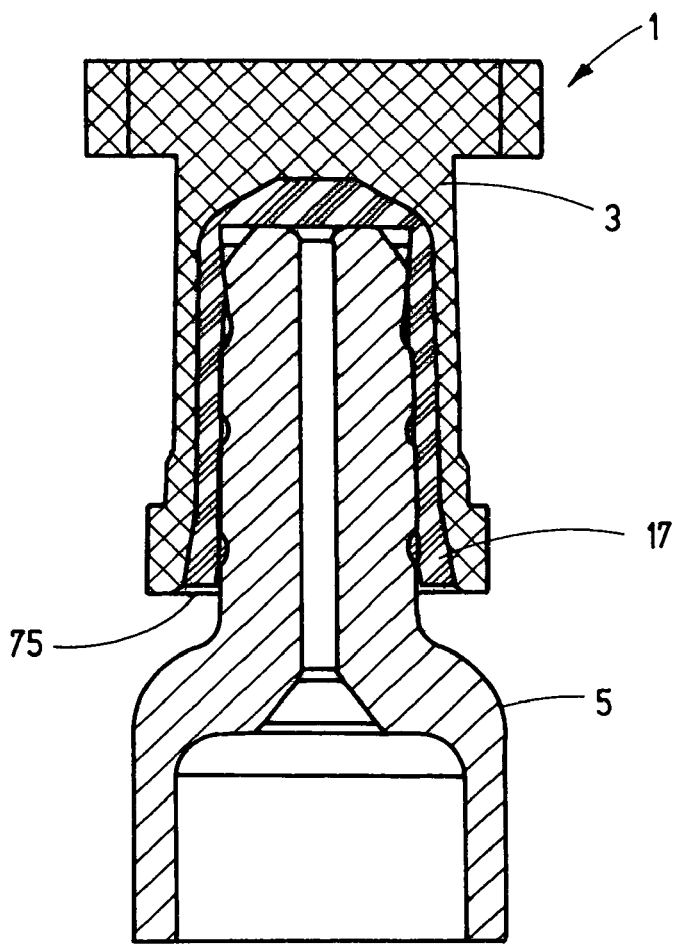
FIG. 10 is a longitudinal sectional view of the attachment according to FIG. 9.

The sectional illustration according to FIG. 10 shows that the attachment 1 has a cap 3, which is entirely enclosed and encompasses the first sealing element 17. The material selection here is the same as in the above examples. The cap 1 is preferably made of hard plastic, while the sealing element 17 is made of rubber or preferably TPE with the specified hardness.

The sections provided with the material of the sealing element in the region of the head 71 are not connected to the inside of the cap 3 in this example, so that during sterilization of the syringe 5 the vapor can penetrate into the inside of the cap 3 only via the lower edge 75 of the sealing element 17 facing the syringe 5 and contribute to optimized sterilization of the attachment 1.

It has been shown that the connection between the cap and sealing element can be implemented particularly easily by means of an injection molding method. Since the cap and the sealing element perform different functions, preferably different materials are selected: the cap comprises hard plastic, or is made of this material in order to protect and support the softer sealing element. The two materials are preferably selected such that they are employed in a two-component injection molding process in order to produce the attachment 1. It has been shown that an ideal connection between the cap and sealing cannot be implemented in all cases. It is therefore particularly preferred to configure the cap 3 such that the sealing element is held on the inside by positive fit.

Incidentally, this also applies to the combination of the second sealing element 45 and the cannula lift 29. The latter is made of a hard plastic, which supports the cannula 19 and receives the second sealing element 45. The element is made of a softer material, preferably rubber or TPE, in order to guarantee the desired sealing properties. In addition, the preferably employed TPE is characterized by excellent vapor permeability, so that the finished, assembled attachment 1 can be easily sterilized.

As was explained based on the cap 3 and the first sealing element 17, when implementing a positive fit between the cap and sealing element, it may be provided that the cap has apertures, through which the material of the first sealing element penetrates at least to the outer surface of the cap 3, preferably extends across it, which becomes particularly apparent based on FIG. 6.

FIG. 6 also shows that the basic principle of molding sealing material into a cap can be implemented both in connection with the cap 3 and the first sealing element 17, and in connection with the cap-shaped cannula lift 29 and the second sealing element 45, wherein preferably a two-component injection molding method is employed, because this method at the same time allows the production of the cap and sealing element.

The invention claimed is:

1. An attachment for a device having a cannula in combination with the device, the attachment comprising:
 a cap including a first end attached to the device and a second end having a first surface formed substantially perpendicular to a longitudinal axis of the cap, the cap including a plurality of webs extending along a longitudinal axis of the cap that define a plurality of openings that extend between adjacent webs, along the longitudinal axis of the cap, and through the first surface; and
 a sealing element attached to the cannula and attached to the cap, the sealing element exposed along a length of the cap and at the first surface by the plurality of openings.

2. The combination according to claim 1, wherein the plurality of openings provide access to the sealing element from an area outside of the cap.

3. The combination according to claim 1, wherein the sealing element projects beyond an outer surface of the cap.

4. The combination according to claim 1, wherein the sealing element extends into the plurality of openings.

5. The combination according to claim 1, wherein the sealing element extends into the plurality of openings along a length of the cap and at the first surface.

* * * * *